United States Patent [19]
Szelejewski et al.

[11] 3,974,207
[45] Aug. 10, 1976

[54] METHOD FOR PRODUCING METHACRYLIC ESTERS

[75] Inventors: Wieslaw Szelejewski, Kedzierzyn; Edward Grzywa, Warsaw; Jerzy Wojciechowski, Kedzierzyn; Kazimerz Fraczek; Zdzislaw Maciejewski, both of Kedzierzyn; Boleslaw Kot, Oswiecim, all of Poland

[73] Assignee: Instyut Ciezkiej Syntesy Organiczej "Blachownia", Kedzierzyn, Poland

[22] Filed: July 9, 1974

[21] Appl. No.: 486,904

[30] Foreign Application Priority Data
July 12, 1973  Poland .................................. 164042

[52] U.S. Cl. .................... 260/486 D; 260/484 R; 260/530 R
[51] Int. Cl.² .................... C07C 67/30; C07C 69/54
[58] Field of Search .................... 260/486 D, 484 R

[56] References Cited
UNITED STATES PATENTS

| | | | |
|---|---|---|---|
| 2,303,842 | 12/1942 | Kirk et al. | 260/486 D |
| 2,360,880 | 10/1944 | Kropa | 260/486 D |
| 3,022,336 | 2/1962 | Sennewald et al. | 260/486 D |
| 3,536,750 | 10/1970 | Holmes et al. | 260/484 |
| 3,678,096 | 7/1972 | Trecker et al. | 260/484 |

FOREIGN PATENTS OR APPLICATIONS

| | | | |
|---|---|---|---|
| 467,433 | 6/1937 | United Kingdom | 260/486 |

*Primary Examiner*—Jane S. Myers
*Attorney, Agent, or Firm*—Haseltine, Lake & Waters

[57] ABSTRACT

This invention relates to a method for producing methacrylic esters from by-products, derived from aldehydes in the Oxo process.

Other esters of methacrylic acid as exemplified by ethyl, propyl and butyl methacrylates can also be obtained.

Isobutyrdehyde is oxidized with oxygen or oxygen-containing gas to isobutyric acid which is then esterified with a $C_1$–$C_4$ aliphatic alcohol and the resulting isobutyric ester is then oxidized in liquid phase with oxygen or oxygen-containing gas to form a hydroxy isobutyric ester derivative which is then subjected to dehydration.

2 Claims, No Drawings

METHOD FOR PRODUCING METHACRYLIC ESTERS

This invention relates to a method for producing methacrylic esters from by-products, derived from aldehydes in the Oxo process.

Up to the present methyl methacrylate has been obtained, in general, according to the acetone cyanohydrin method, based on acetone and hydrogen cyanide. The main shortcoming of this method is the considerable consumption of concentrated sulfuric acid. Usually, about two tons of sulfuric acid per one ton of product are consumed in the process, leaving considerable amounts of burdensome waste material. In spite of mass production, the cost of producing methyl methacrylate by this method is relatively high.

Another known method of producing methacrylic esters is based on esterification of methacrylic acid with alcohols, where the methacrylic acid is obtained by oxidizing isobutylene or from methacrylonitrile.

However, considering the low yield of the process of producing methacrylic acid and the difficulties arising in the polymerization of intermediates, the said method is applied in industry only to a very small extent.

There are also other known patented methods concerning the production of methacrylic esters obtained by oxidative dehydrogenation of isobutyric acid esters.

The method referred to in German Patent No. 1,286,022 relates to the production of methacrylic esters by subjecting the isobutyric acid esters to dehydrogenation, in the vapor phase at 450° – 500°C, in the presence of iodine catalyst promoted by oxygen and on a corresponding magnesium silicate heating medium.

U.S. Pat. No. 3,721,705 and French Pat. No. 2,096,318 describe a method of producing methacrylic acid and its esters, which consists in dehydrogenation of isobutyric acid or esters thereof by using sulfur at a temperature of 500°C.

German Patent application No. 2,208,580 proposes a method of dehydrogenating methyl isobutyrate to form methyl methacrylate by using a mixture of sulfur vapor and hydrogen sulfide, wherein the process is conducted at 500°C in a reactor using Raschig rings packing.

The latter methods of producing methacrylic esters have as yet no practical use, because of the high temperatures in the dehydrogenation reaction.

The process is accompanied by various side-reactions, resulting in the formation of compounds, which render the purification of the final product difficult, forming at the same time a great amount of waste products.

The aim of the invention is to develop a more economically advantageous and reliable method of producing methacrylic acid esters from isobutyraldehyde, being a by-product in the Oxo process, which has been converted partly to isobutyl alcohol or recycled to the process or directed for burning out, using new and easily available feed sources.

It has been found that methyl methacrylate or other, methacrylic acid esters can be obtained in good yields from isobutyraldehyde by oxidation to isobutyric acid, esterification of isobutyric acid to the corresponding esters by means of alcohols, oxidation of the ester to the alpha-hydroxyisobutyrate and dehydration of the alpha-hydroxyisobutyrate to the methacrylate of the corresponding alcohol.

Though the method of the present invention and the claimed scope are not intended to be limited to the product of methyl methacrylate only, the further description will be, for reason of simplification directed to producing said compound only.

Obviously, by the method according to the present invention, there can also be obtained other esters of methacrylic acid as exemplified by ethyl, propyl and butyl methacrylates.

According to the invention isobutyraldehyde is oxidized to isobutyric acid in the liquid phase by means of oxygen or an oxygen-containing gas, e.g. air at a temperature of 20°–120°C in the presence or absence of a catalyst under a pressure of 0 to 10 atmospheres and the unreacted isobutyraldehyde, after distilling off is recycled to the process.

The isobutyric acid is then esterified with methanol in the known manner at a temperature of 50 to 100°C in the presence of sulfuric acid catalyst, whereupon the mixture on esterification is separated by distillation and the resulting methyl isobutyrate in liquid phase is oxidized to methyl alpha-hydroxyisobutyrate with oxygen or an oxygen-containing gas, such as air at a temperature of 50 to 150°C under a pressure of 0 to 30 atmospheres.

The oxidation process can be conducted in the absence or presence of catalysts such as organic metal salts, wherein the metal is selected from the groups VIB, VIIB and VIIIB of the periodic chart of elements, such as acetates, butyrates, naphthenates of Co, Mn, Cu, and Ni, and the like and with or without addition of promoters such as acetaldehyde and methyl ethyl ketone or bromide promoters such as barium bromide or lead bromide. The oxidation process can also be effected in organic solvents, preferably in butyric acid and isobutyric acid solvents.

The oxidation process of methyl isobutyrate to methyl alpha-hydroxyisobutyrate can also be effected by use of organic peroxides, such as benzoyl peroxide or the organic peroxide promoters can be also introduced when oxidizing with air.

The oxidation products are separated by distillation while isolating methyl alpha-hydroxyisobutyrate, the unreacted isobutyrate and other products such as isobutyric acid and isobutyraldehyde are recycled to the process.

The isolated methyl alpha-hydroxyisobutyrate is subjected to dehydration in the liquid phase at a temperature of 60 to 140°C in the presence of a sulfonated cation exchanger in a column system under a pressure of 200–760 mm Hg with the addition of polymerization inhibitors, e.g. hydroquinone. The dehydration reaction can also be conducted in the vapor phase over heterogeneous catalysts such as reactive aluminum oxide or aluminum silicates. The post-reaction mixture is separated by rectification, recovering methyl methacrylate and the unreacted hydroxyisobutyrate is recycled to the process.

The oxidation process of isobutyraldehyde and methyl isobutyrate can also be conducted simultaneously and the isobutyraldehyde is introduced into the system continuously.

Unreacted methyl isobutyrate and isobutyraldehyde are separated by distillation from the mixture and recycled to the process, while the mixture of isobutyric acid and methyl alpha-hydroxyisobutyrate is esterified, methyl isobutyrate is separated by rectification and oxidized and alpha-hydroxyisobutyrate is processed as described above.

The method according to the present invention assures the utilization of new feed sources for the production of methyl methacrylate and is characterized by high chemical yields. Contrary to the hitherto used techniques only some minor amounts of waste water and waste products are obtained. The economics of waste water and waste products are obtained. The economics of the process according to this invention is extremely advantageous when compared with the techniques used hitherto, as easily available and cheap raw materials are applied.

EXAMPLE I 40.0 g isobutyraldehyde was oxidized with oxygen at 40°C in a column-type barbotage reactor at atmospheric pressure during 5 hours; the flow of oxygen amounted to 0.2 1/min.

The reaction mixture was subjected to distillation and 2.0 g of isobutyraldehyde obtained was recycled to the next run, and 46.5 g isobutyric acid esterified with excess of methanol in the presence of 1% w/w $H_2SO_4$ during 4 hours at 60°C. Distillation of the product of esterification gave 48.0 g of methyl isobutyrate.

The methyl isobutyrate obtained and the methyl isobutyrate recycled were oxidized with oxygen at 90°C in a columntype barbotage reactor under atmospheric pressure during 10 hours in the presence of 0.1 % w/w benzoyl peroxide fed by portions.

55.8 g alpha-hydroxyisobutyrate obtained were separated by distillation from 503.0 g methyl isobutyrate and isobutyric acid recycled to the oxidation stage.

Alpha-hydroxyisobutyrate was dehydrated on a sulfonated cation exchanger charged with 100 g per hour alpha-hydroxyisobutyrate on 100 ml of the cation exchanger at a temperature of 100°C at 760 mm Hg in a column-type reactor in the presence of 0.1 % hydroquinone.

The 26.9 g methyl methacrylate were obtained as 54% of the theoretical yield in relation to isobutyraldehyde separated by distillation from 44.2 g of alpha-hydroxyisobutyrate which was recycled and from 28.9 g of side-products.

EXAMPLE II

To a column-type barbotage reactor of 6 l capacity methyl isobutyrate, isobutyraldehyde, air and Co-acetate as a catalyst were continuously fed at the rates of 830 g/h, 82.5 g/h, 120 l/h and 150 mg/h, respectively. The reaction temperature amounted to 120°C and pressure to 5 atmospheres. The distillation of the product gave 4.0 g/h of isobutyraldehyde and 638 g/h of methyl isobutyrate which were recycled to the process and 265 g/h of the mixture of isobutyric acid and alpha-hydroxyisobutyrate, containing 30% of the former and 38% of the latter, which were esterified.

The esterification was performed continuously in a column system with $V_{eff}$ = 40 ml giving 350 g/h of the product which continuously distilled yielded 112 g/h of alpha-hydroxyisobutyrate and 190 g/h methyl isobutyrate recycled to oxidation.

The alpha-hydroxyisobutyrate was dehydrated in a column type reactor $V_{eff}$ = 1000 ml packed with 300 ml of a sulfonic acid cation exchanger at a temperature of 100°C and a pressure of 700 mm Hg in the presence of 0.1 % w/w hydroquinone giving 87.1 g/h product consisting of: 24.3 % w/w acetone, 63.9% w/w methyl methacrylate, 11.5% w/w water and 0.3% w/w of others. The product was distilled giving 53.8 g/h methyl methacrylate i.e. 50% of the theoretical yield in relation to isobutyraldehyde.

EXAMPLE III 46.5 g isobutyric acid obtained by oxidizing isoburyraldehyde as in Example I, were esterified with excess ethanol and under the conditions as in Example I. The esterification product was subjected to distillation and 53 g ethyl isobutyrate was obtained.

The ethyl isobutyrate formed was oxidized with oxygen at 90°C in a column-type barbotage reactor at atmospheric pressure during 10 hours in the presence of 0.1% w/w benzoyl peroxide.

62 g ethyl alpha-hydroxyisobutyrate obtained were dehydrated on a sulfonated cation exchanger under conditions as in Example I. 34 g ethyl methacrylate were separated by distillation from the dehydration product.

EXAMPLE IV 47 g isobutyric acid obtained by oxidation of isobutyraldehyde as in Example I was esterified with excess propanol under conditions as in Example I. Propyl isobutyrate was separated from the post-esterification mixture and 60.0 g product were obtained.

The propyl isobutyrate was oxidized with oxygen at 90°C in a column-type barbotage reactor under atmospheric pressure during 10 hours. 69 g propyl alpha-hydroxyisobutyrate were obtained. The propyl alpha-hydroxyisobutyrate was oxidized with oxygen at 90°C in a column-type barbotage reactor as in Example III and the propyl alpha-hydroxyisobutyrate was dehydrated on a sulfonated cation exchanger. 56 g propyl methacrylate were obtained.

EXAMPLE V 47 g isobutyric acid were esterified with excess n-butanol under conditions as in Example I and 67 g butyl isobutyrate were obtained. Butyl isobutyrate was oxidized with oxygen under conditions as in Example I.

74 g butyl alpha-hydroxyisobutyrate were separated from the oxidation products. Butyl alpha-hydroxyisobutyrate was dehydrated on a sulfonated cation exchanger and 37.4 g butyl methacrylate were obtained.

What we claim is:

1. A method of producing a $C_1$–$C_4$ alkyl methacrylate which comprises the steps of (1) oxidizing isobutyroldehyde to isobutyric acid with oxygen or an oxygen-containing gas in the liquid phase at 20° to 120°C. in the presence or absence of a catalyst to form isobutyric acid, (2) esterifying the isobutyric acid with a $C_1$–$C_4$ aliphatic alcohol at 50 to 100°C. in the presence of sulfuric acid as a catalyst to form the $C_1$–$C_4$ alkyl isobutyrate (3) oxidizing the $C_1$–$C_4$ alkyl isobutyrate in the liquid phase with oxygen or an oxygen-containing gas at 50° to 150°C. in the presence or absence of a catalyst to form the $C_1$–$C_4$ alkyl alpha-hydroxyisobutyrate and (4) dehydrating the $C_1$–$C_4$ alkyl alpha-hydroxyisobutyrate in the liquid phase at 60° to 140°C. in the presence of a sulfonated cation-exchange resin and a polymerization inhibitor to form the $C_1$–$C_4$ alkyl methacrylate.

2. A continuous method of producing a $C_1$–$C_4$ alkyl methacrylate which comprises simultaneously oxidizing a mixture of isobutyraldehyde and a $C_1$–$C_4$ alkyl isobutyrate in the liquid phase with oxygen or an oxygen-containing gas at a temperature of 20° to 120°C. in the presence or absence of a catalyst to form a mixture of isobutyric acid and $C_1$–$C_4$ alkyl alphahydroxyisobutyrate, recycling unreacted isobutyraldehyde and $C_1$–$C_4$ alkyl isobutyrate to the initial reaction mixture, treating the mixture of isobutyric acid and $C_1$–$C_4$ alkyl alpha-hydroxyisobutyrate with a $C_1$–$C_4$ aliphatic alcohol at 50° to 100°C. in the presence of sulfuric acid as a catalyst to form a mixture of $C_1$–$C_4$ alkyl isobutyrate and $C_1$–$C_4$ alkyl alpha-hydroxy-isobutyrate, recycling the $C_1$–$C_4$ alkyl isobutyrate to the initial reaction mixture, dehydrating the $C_1$–$C_4$ alkyl alpha-hydroxy-isobutyrate in the liquid phase at 60° to 140°C. in the presence of a sulfonated cation-exchange resin and a polymerization inhibitor to form the $C_1$–$C_4$ alkyl methacrylate and continuously introducing isobutyraldehyde into the initial reaction mixture.

* * * * *